US012178956B2

(12) United States Patent
Bartels et al.

(10) Patent No.: US 12,178,956 B2
(45) Date of Patent: Dec. 31, 2024

(54) INHALATION DEVICE

(71) Applicant: INVOX BELGIUM NV, Diepenbeek (BE)

(72) Inventors: Frank Bartels, Hattingen (DE); Juergen Rawert, Cologne (DE)

(73) Assignee: INVOX BELGIUM NV, Diepenbeek (BE)

( * ) Notice: Subject to any disclaimer, the term of this patent is extended or adjusted under 35 U.S.C. 154(b) by 994 days.

(21) Appl. No.: 16/973,789

(22) PCT Filed: Jul. 12, 2019

(86) PCT No.: PCT/EP2019/068866
§ 371 (c)(1),
(2) Date: Dec. 10, 2020

(87) PCT Pub. No.: WO2020/016135
PCT Pub. Date: Jan. 23, 2020

(65) Prior Publication Data
US 2021/0252234 A1 Aug. 19, 2021

Related U.S. Application Data

(60) Provisional application No. 62/698,401, filed on Jul. 16, 2018.

(30) Foreign Application Priority Data

Jul. 16, 2018 (EP) .................................... 18183726

(51) Int. Cl.
*A61M 11/00* (2006.01)
*A61M 15/00* (2006.01)
*B05B 11/10* (2023.01)

(52) U.S. Cl.
CPC ...... *A61M 11/007* (2014.02); *A61M 15/0065* (2013.01); *B05B 11/109* (2023.01);
(Continued)

(58) Field of Classification Search
CPC ............ A61M 11/007; A61M 2202/04; A61M 2205/276; A61M 2205/8281;
(Continued)

(56) References Cited

U.S. PATENT DOCUMENTS

| | | | | |
|---|---|---|---|---|
| 5,713,349 A | 2/1998 | Keany | | |
| 6,945,472 B2 * | 9/2005 | Wuttke | B05B 11/1091 | 239/324 |

(Continued)

FOREIGN PATENT DOCUMENTS

| | | |
|---|---|---|
| CA | 2459278 A1 | 3/2003 |
| CN | 1081155 A | 1/1994 |

(Continued)

OTHER PUBLICATIONS

Written Opinion of the International Application PCT/EP2019/068866, Sep. 18, 2019, 6 pages.

*Primary Examiner* — Tu A Vo
(74) *Attorney, Agent, or Firm* — Synergy IP Group AG

(57) ABSTRACT

An inhalation device including a housing; a reservoir for storing a liquid; a pumping unit including a riser pipe; a hollow cylindrical part having an interior space and being linearly moveable on the riser pipe, the pumping chamber fluidically connected with the reservoir; a nozzle connected liquid-tight to a downstream end portion of the riser pipe; wherein the linear relative motion can be effected by a relative rotation around a rotational axis of a rotatable part with respect to a counterpart converting the relative rotation into the linear relative motion by a gear mechanism comprising at least one cam surface having a first section and a (Continued)

second section, a spring for the storage of potential energy, wherein the cam surface has, between the first section and the second section, a third section of constant height upon which no linear relative motion occurs while the counterpart slides along it.

14 Claims, 5 Drawing Sheets

(52) U.S. Cl.
CPC ...... *B05B 11/1091* (2023.01); *A61M 2202/04* (2013.01); *A61M 2205/276* (2013.01); *A61M 2205/8281* (2013.01)

(58) Field of Classification Search
CPC .............. A61M 15/0065; A61M 11/00; A61M 11/006; A61M 11/08; B05B 11/109; B05B 11/1091
See application file for complete search history.

(56) References Cited

U.S. PATENT DOCUMENTS

2003/0042336 A1* 3/2003 Wuttke ............. A61M 15/0065 239/569
2003/0078551 A1* 4/2003 Hochrainer .......... A61M 11/006 604/295
2004/0026458 A1 2/2004 Fuchs
2005/0269424 A1* 12/2005 Wuttke .................. A61M 11/06 239/321
2008/0105702 A1 5/2008 Mochizuki et al.
2010/0145275 A1* 6/2010 Grunhut .............. B05B 11/1091 604/131
2010/0288277 A1 11/2010 Gordon et al.
2012/0260913 A1* 10/2012 Bach .................... B65D 83/384 128/200.21
2017/0361038 A1 12/2017 Mayer et al.

FOREIGN PATENT DOCUMENTS

| | | | |
|---|---|---|---|
| CN | 1493408 | A | 5/2004 |
| CN | 101039714 | A | 9/2007 |
| CN | 105378761 | A | 3/2016 |
| EP | 0627230 | B1 | 2/2000 |
| EP | 1427538 | B1 | 7/2008 |
| JP | H11512649 | A | 11/1999 |
| JP | 2005501621 | A | 1/2005 |
| JP | 2007520349 | A | 7/2007 |
| RU | 2495726 | C2 | 10/2013 |
| WO | 9315845 | | 8/1993 |
| WO | 9417370 | A2 | 8/1994 |
| WO | 9712687 | | 4/1997 |
| WO | 9712687 | A1 | 4/1997 |
| WO | 03020436 | A1 | 3/2003 |
| WO | 2005075105 | A1 | 8/2005 |
| WO | 2007128381 | A1 | 11/2007 |
| WO | 2009090084 | A1 | 7/2009 |
| WO | 2015006292 | A1 | 1/2015 |
| WO | 2018048786 | A1 | 3/2018 |
| WO | 2018197730 | A1 | 11/2018 |

* cited by examiner

INHALATION DEVICE

CROSS REFERENCE TO RELATED APPLICATIONS

This application is a United States National Stage Application filed under 35 U.S.C. § 371 claiming priority to and the benefit of PCT Application No. PCT/EP2019/068866, filed on Jul. 12, 2019, which claims priority to and the benefit of European Application No. 18183726.1, filed on Jul. 16, 2018, and U.S. Provisional Application Ser. No. 62/698,401, filed on Jul. 16, 2018, all of which are incorporated herein by reference in their entireties.

FIELD OF THE INVENTION

The invention relates to the field of inhalation devices for liquids. In particular, the invention relates to a liquid emission mechanism for an inhalation device, as well as a method of emitting a liquid from an inhalation device.

BACKGROUND OF THE INVENTION

Nebulizers or other aerosol generators for liquids are known from the art since a long time ago. Amongst others, such devices are used in medical science and therapy. There, they serve as inhalation devices for the application of active ingredients in the form of aerosols, i.e. small liquid droplets embedded in a gas. Such an inhalation device is known e.g. from document EP 0 627 230 B1. Essential components of this inhalation device are a reservoir in which the liquid that is to be aerosolized is contained; a pumping unit for generation of a pressure being sufficiently high for nebulizing; as well as an atomizing device in the form of a nozzle.

An improvement of such an inhalation device is disclosed in patent application PCT/EP2018/061056, filed by the same applicant as the present invention, the content of which is incorporated herein in its entirety.

A typical liquid emission mechanism comprises a means for the storage of potential energy such as a spring, and a gear unit. By (preferably manually) loading the spring, potential energy is stored in the inhalation device. The energy can subsequently be used for generating a pressure inside a pumping chamber which is fluidically connected to the nozzle.

Document WO 2007/128381 A1 discloses another atomization device for medically active liquids comprising a liquid emission mechanism. Relative rotation of two parts of the housing is transferred by means of said gear unit into a linear motion, which is then used for loading a spring. This motion transfer is achieved by using at least one pair of helical surfaces which glide along each other. After a complete loading rotation which, when two pairs are present, amounts to 180 degrees, the initially axially rising surfaces each provide a sharp edge with an (also axially) vertical drop. The length of said drop corresponds to the pumping motion of the pumping device. Thus, when the edges pass each other by attempting to further rotate the mechanism, the axial motion is reversed and the potential energy is released again, resulting in a pressure generation.

Care must be taken in order to prevent the premature and undesired release of said potential energy. For this, solutions known in the art provide a locking element that stops rotation just when both sliding surfaces reach said edges. In other words, just when said further rotation would result in said "drop", said locking element prevents any axial motion. By manually de-activating said locking element (i.e. by pushing a release button), the potential energy is intentionally released and used for the generation of pressure.

In WO 2007/128381 A1, a small amount of liquid is already pumped through the liquid filled ducts (pumping chamber, nozzle) when priming the device. By axially offsetting the locking mechanism such that, when reaching the end of the rotating loading motion, the edges in fact just pass each other, resulting in a partial motion along aforesaid "drop", and in a pre-emission of liquid due to the beginning axial movement of the pumping mechanism. After a short distance, the offset locking mechanism ends said motion. Only upon subsequent actuation, which occurs by an activation (release) of the locking mechanism, the full pumping motion is performed and the desired dose of liquid is atomized.

A drawback of said premature pumping effect is that the amount of liquid that is emitted prior to the actual dosing must be discharged from the nozzle exit before the actual atomization starts. Otherwise, clogging of the nozzle exits can result in undesired droplet formation, and/or a generation of splashes. Further, the amount of liquid required for the premature pumping reduces the overall number of possible dosing cycles per reservoir. Also, the aforesaid "drop" results in a well audible clicking sound which can be perceived as being irritating for some users.

A further drawback is that the constructional effort to provide a locking element of the aforementioned type is high, resulting in higher production and assembly costs as well as an increased probability of mechanical failure.

SUMMARY OF THE INVENTION

In first aspect, the present invention provides an inhalation device for medically active liquids for generation of an aerosol, comprising

- a housing, inside this housing a reservoir for storing a liquid, a pumping unit, said unit comprising a riser pipe, a hollow cylindrical part having an interior space configured to receive an upstream end portion of said riser pipe, said cylindrical part being linearly moveable on the riser pipe, wherein the cylindrical part and the riser pipe form a pumping chamber having, by means of linear relative motion of the cylindrical part with respect to the riser pipe, a variable volume for generation of a pressure inside said pumping chamber, wherein
- the pumping chamber is fluidically connected with the reservoir and with a nozzle which is connected liquid-tight to a downstream end portion of the riser pipe, and wherein
- said linear relative motion can be effected by a relative rotation around a rotational axis of a rotatable part which is part of, or connected to, a first part of the housing with respect to a counterpart which is part of, or connected to, a second part of said housing, such that said relative rotation is converted into said linear relative motion by means of a gear mechanism, said gear mechanism comprising at least one cam surface comprising, in axial direction, a first section of increasing height as well as a second section of decreasing height, the cam surface being capable of sliding along an adjacent counterface, wherein the cam surface is, upon rotation, adapted to slide along said counterface, resulting in said conversion, and wherein
- a means for the storage of potential energy is provided which is chargeable by means of said relative rotation along the first section, and wherein said energy is releasable to said pumping device when released, and wherein said cam surface comprises, between the first section of increasing height and the second section of decreasing height, a third section of constant height, such that, while said third section of said cam surface slides along the counterface, no linear relative motion of the cylindrical part with respect to the riser pipe occurs, and wherein a dosing cycle which covers the rotation angle of the first, the second, and the third section, corresponds to a rotation of 180 degrees.

In a second aspect, the present invention provides a method for the generation of an aerosol by means of an inhalation device according to any one of the preceding claims, wherein the method comprises, upon rotation of the rotatable part, a first, charging phase for filling the pumping chamber with liquid, and a second, discharging phase for emitting the atomized liquid from the nozzle, wherein between said two phases, a third, resting phase exists during which, despite further rotation, the volume of the pumping chamber remains constant.

OBJECT OF THE INVENTION

The object of the invention is the provision of a device that avoids the drawbacks of the known art.

The invention shall provide a possibility of preventing any premature and undesired release of liquid from the nozzle, as well as avoid a reduction of dosing cycles per reservoir.

The invention shall also provide a cost effective and mechanically reliable solution.

DESCRIPTION OF THE INVENTION

According to the first aspect of the invention, the object is solved by an inhalation device for medically active liquids for generation of an aerosol, comprising a housing, inside this housing a reservoir for storing a liquid, a pumping unit, said unit comprising a riser pipe, a hollow cylindrical part having an interior space configured to receive an upstream end portion of said riser pipe, said cylindrical part being linearly moveable on the riser pipe, wherein the cylindrical part and the riser pipe form a pumping chamber having, by means of linear relative motion of the cylindrical part with respect to the riser pipe, a variable volume for generation of a pressure inside said pumping chamber, wherein the pumping chamber is fluidically connected with the reservoir and with a nozzle which is connected liquid-tight to a downstream end portion of the riser pipe, and wherein said linear relative motion can be effected by a relative rotation around a rotational axis of a rotatable part which is part of, or connected to, a first part of the housing with respect to a counterpart which is part of, or connected to, a second part of said housing, such that said relative rotation is converted into said linear relative motion by means of a gear mechanism, said gear mechanism comprising at least one cam surface comprising, in axial direction, a first section of increasing height as well as a second section of decreasing height, the cam surface being capable of sliding along an adjacent counterface, wherein the cam surface is, upon rotation, adapted to slide along said counterface, resulting in said conversion, and wherein a means for the storage of potential energy is provided which is chargeable by means of said relative rotation along the first section, and wherein said energy is releasable to said pumping device when released, and wherein said cam surface comprises, between the first section of increasing height and the second section of decreasing height, a third section of constant height, such that, while said third section of said cam surface slides along the counterface, no linear relative motion of the cylindrical part with respect to the riser pipe occurs, and wherein a dosing cycle which covers the rotation angle of the first, the second, and the third section, corresponds to a rotation of 180 degrees.

Furthermore, the object is solved by the method according to second aspect of the invention. Advantageous embodiments are described in the respective dependent claims, the subsequent description, as well as the accompanying figures.

The inhalation device serves for the generation of an aerosol medically from active liquids for inhalation therapy. In particular, the inhalation device is adapted for the dose-wise generation and emission of nebulized aerosols suitable for the pulmonary delivery of medically active ingredients.

Typically, such an inhalation device comprises a housing, inside this housing a reservoir for storing a liquid, and a pumping unit which is preferably based on the principle of a piston pump, or plunger pump. More specifically, said pumping unit according to the invention comprises a hollow cylindrical part having an interior space for generation of a pressure inside a pumping chamber. It is noted that the term "cylindrical part" refers to a part having a cylindrical internal surface; the outside as well as a portion which does not come in contact with the riser pipe and/or the seal do not have to be cylindrical.

The pumping chamber is formed by the cylindrical part and a riser pipe and has a variable volume for generation of a pressure inside said pumping chamber. The pumping chamber is fluidically connected with the reservoir; optionally, via a check valve which blocks in direction of the reservoir. To achieve the volume variability, said riser pipe can be received with at least one reservoir-facing, interior end (subsequently called "upstream end portion") in said cylindrical part, and the cylindrical part is linearly moveable on the riser pipe.

A nozzle is connected liquid-tight directly or indirectly to a downstream end portion of the riser pipe.

The riser pipe can be immobile with respect to the housing of the device, or at least to a part of the housing to which also the nozzle is firmly affixed, directly or indirectly, so that the riser pipe is also immobile or unmoveable relative to the nozzle. In another embodiment, the riser pipe is moveable, and the pumping chamber/cylindrical part is immobile with respect to said housing. In yet another embodiment, both cylindrical part and riser pipe are moveable.

In other words, the cylindrical part has an interior space configured to receive an upstream end portion of said riser pipe. The cylindrical part is configured to be linearly moveable along said end portion such that the volume inside said cylindrical part is changeable by means of linear relative motion of said riser pipe or vice versa.

Further, said linear relative motion can be effected by a relative rotation around a rotational axis of a rotatable part which is part of, or connected to, a first part of the housing with respect to a counterpart which is part of, or connected to, a second part of said housing, such that said relative rotation is converted into said linear relative motion by means of a gear mechanism or the like. Thus, the housing comprises two parts, one of them being able to rotate relative to the other. The gear mechanism comprises at least one cam surface, i.e. a surface which is capable of sliding along an adjacent counterface or another corresponding component, which is guided by the specific shape of the cam surface. The cam surface may be in the form of a track running around the rotational main axis of the device in a curved manner. Specifically, the cam surface may be in the form of a closed or endless track running around the rotational main axis in a circular or circumferential manner as described in further detail below.

This cam surface has or comprises, in axial direction, a first section of increasing height as well as a second section of decreasing height. Here, the axial direction is a direction which runs parallel to (or is identical with) the longitudinal direction of the pumping chamber/cylindrical part. Upon relative rotation of the part which carries the cam surface and the part which carries the counterface, the cam surface can slide along said counterface, resulting in said conversion. During said sliding, cam surface and counterface remain in axial contact. As a result, by relative rotation of the rotatable part with respect to the counterpart, the volume of the pumping chamber is changed. Motion along the first section results in an increase of volume (and thus a decrease of pressure in the pumping chamber, and of filling the same with liquid from the reservoir), and motion along the second section results in a decrease of volume (and an increase of pressure in the pumping chamber, and emission of liquid from the nozzle). It is clear that, depending on the actual construction, the opposite effects can be obtained as well. However, for the sake of clarity, the effects of the respective sections on the volume are defined as stated before.

In other words, a first part of the gear has a cam surface and is connected to a first part of the housing; and a second part (counterpart) of the gear has a counterface and is connected to a second part of the housing; and the first part and the second part are rotatable relative to one another such that the cam surface and the counterface slide on one another.

Further, a means for the storage of potential energy is provided which is chargeable by means of said relative rotation along the first section, and said energy is releasable to said pumping device when released, e.g. by activation of a release means. Preferably, said means for the storage is provided by an elastic spring. By tensioning said spring, potential energy is stored, and by allowing it to re-contract, the energy is released. In another embodiment, the effects are inverse (compression spring).

According to the invention, said cam surface has or comprises, between the sections of increasing and decreasing height, a third section of constant, or almost constant, height, such that, while said counterface slides along said third section, no, or almost no, linear relative motion occurs.

As a result, a rotation of the rotatable part along the third section which is arranged between the first and the second section will not change the relative axial position of rotatable part and counterpart, and thus, of the volume within the pumping chamber, and thus, will not change its inside pressure. At the same time, the loading state of the means for the storage of potential energy is also not changed by this rotation along the third section. In this phase, no premature pumping of liquid occurs, and therefore no liquid is emitted prior to the actual dosing. No clogging of the nozzle exits due to pre-emission of liquid takes place, avoiding undesired droplet formation, and a generation of splashes. Further, the overall number of possible dosing cycles per reservoir is increased, and the aforementioned clicking sound may be avoided, if necessary or desired. Also, a blocking means which might be provided to prevent unintentional actuation of the device can be constructed in a more simple manner, resulting in decreased production and assembly costs as well as an decreased probability of mechanical failure.

In one embodiment, the cam surface is arranged at, or connected to, the rotatable part, and the counterpart provides the counterface.

In another embodiment, the cam surface is arranged at, or connected to, the counterpart, and the rotatable part provides the counterface.

It is noted that the term “counterface” is to be interpreted broadly, such that every type of component that serves for the purpose of providing a gliding interaction with the cam surface falls under the present definition.

In one embodiment, the counterface is provided by a second cam surface. Thus, two cam surfaces exist, both simultaneously serving as the respective counterfaces. In other words, the counterpart (or conversely, the rotatable part) provides a cam surface as well, and particularly, a surface having the inverted shape of the according cam surface of the rotatable part (or conversely, the counterpart), or one or more segments thereof. This results in a maximal mechanical overlap of both parts, reducing mechanical wear.

In another embodiment, in one part, one cam surface is present, but instead of a second cam surface, the second part (the rotatable part or the counterpart) provides a corresponding cam.

In yet another embodiment, instead of the cam, the rotatable part or the counterpart can provide a roller or the like for physical interaction with the corresponding cam surface, providing exceptionally low friction, and therefore possibly reducing the force which is necessary for charging the device.

However, all aforementioned embodiments have essentially comparable effects, namely ensuring a variable relative axial position of rotatable part and counterpart upon relative rotation of these parts.

When each section of the cam surface is projected onto a plane which is perpendicular to the rotational axis (“rotation plane”), an individual rotation angle can be assigned to each section.

Thus, one dosing cycle covers or comprises the respective rotation angle of the first, the second, and the third section and optionally further sections, such as the optional fourth section as described below or an optional fifth section, preferably of constant height, which may follow the second section. One dosing cycle can be defined as a “series” of said sections.

In one embodiment of the inhalation device, with regard to a complete cycle, a 360 degree rotation covers two complete series of all these sections at least once. This means that, when rotating the rotatable part by 360 degrees, all respective sections, namely the first, the second, the third and potentially a fourth or fifth section are passed for two times.

In other words, the sums of the respective rotation angles, measured in said rotation plane around the rotation axis from a beginning to an end of the respective section, amount to 360 degrees, or to a whole-number fraction thereof. This means that, depending on the embodiment, a full 360 degree rotation is required to pass all sections and thus, to load and discharge one dose of liquid, or e.g. ½, ⅓, . . . of said 360 degrees, i.e. 180, 120, . . . degrees.

In a preferred embodiment, the sums of the respective rotation angles, measured in said rotation plane around the rotation axis from a beginning to an end of the respective section, amount to 180 degrees, or to a whole-number fraction thereof. This means that, depending on the embodiment, a 180-degree rotation is required to pass all sections and thus, to load and discharge one dose of liquid, or e.g. the half or a third or another fraction of said 180 degrees, i.e. 90, 60, . . . degrees or another angle depending on the number of doses to be emitted per 180 degree rotation.

Accordingly, two doses are emitted on a rotation of 360 degrees, meaning that one dose is loaded and emitted on half a complete rotation corresponding to 180 degrees. Other preferred whole numbers are three and four.

If an optional fourth and/or fifth section (such as another section of constant height, or a section intended to inhibit further rotation of the rotatable part) is present additionally between or following the aforesaid sections, and in particular, between the second and the first section (i.e. the first section is preceded by said fourth section), or between the third section and the second section (i.e. the fourth section provides a differently shaped "end" of the third section) or after the end of the second section e.g. in the form of a further section of constant hight following the second section, it is clear that the aforesaid is true for all four or five sections, i.e. a full dosing cycle of 180 degrees covers all four or five sections, etc.

The advantage of a 180 degree rotation for one dosing cycle is that the slope of the first section can still be lower, since more (rotational) path is provided in order to obtain a desired linear relative motion to generate a sufficient pressure while two dosing cycles can be realized with one full rotation. This is advantageous if the pressure must be exceptionally high, the dosing volume is large, or the force available for rotation is low (e.g. when the device is to be operated by children) while a full rotation of 360 degrees cannot be realized, for example, due to construction or design restrictions.

A fractional rotation for one dose is preferred in other cases.

As outlined above, the sum of the rotation angles of one pumping cycle as defined before amounts to 180 degrees. A rotation of 180 degrees for each dosing cycle has proven to be a good compromise with regard to force necessary for operation, and achievable pressure/volume for said dose. In this case, furthermore, in specific embodiments the rotation angle of the third section, i.e. the section with constant or substantially constant height, amounts to 7±6 degrees, or in other words from 1 to 13 degrees. Experiments have shown that this range is particularly useful in practice. If the third section's angle is too small, such as less than 1°, it becomes increasingly difficult to stop the rotation immediately at the end of this section. On the other hand, larger third sections waste precious room available for other rotation phases, in particular, the first section which is required for building up the pressure and thus must not be too short/steep.

In another embodiment, the rotation angle of the second section, i.e. the section with decreasing height, amounts to 0 degrees, resulting in an axially oriented section of the cam surface. In other words, after passing the edge of the third section, the adjacent part abruptly "drops" back to the beginning of the first section, allowing the instant release of the stored energy, resulting in a sudden pressure increase within the pumping chamber. Note that the term "drop" does only refer to a reduction of the axial position of rotatable part with respect to the counterpart, but does not denote a specific spatial direction. The same is true for the terms "up" and "down", where used.

However, due to the limited amount of liquid that can pass through the nozzle, the volume will decrease over a certain period of time ("emission time"). Thus, depending on the concrete construction, the respective part might not reach its initial position (almost) immediately, and a somehow "undefined" interim state of its position might occur in which the cam surface and the counterface may temporarily lose contact. Therefore, in another embodiment, said rotation angle amounts to a value of more than 0 degrees, such as 1, 2 or 3 degrees. As a result, the respective part does not "drop", but is still guided along the cam surface even during the discharge phase, which can enhance stability of the dosing function.

In specific embodiments in which one pumping cycle as defined above amounts to 180 degrees, the rotation angle of the first section (the section with increasing height) may amount to a value of up to about 170 degrees, such as a value in the range from about 150 to 170 degrees or from about 155 to about 165 degrees. In these embodiments, furthermore, the rotation angle of the second section (the section with decreasing height) amounts to a value in the range from about 0 to about 3 degrees or from about 0 to about 2 degrees or to about only 1 degree. Furthermore, in these embodiments the rotation angle of the third section (the section with substantially constant height) amounts to a value in the range from about 1 to about 13 degrees or from about 3 to about 11 degrees or from about 5 to about 9 degrees, or from about 6 to about 8 degrees. It should be noted, however that additional fourth and fifth sections may be present between the first, second and third section or after the second section. In specific embodiments, a fifth section is present following the third section (thereby preceding the first section of the following dosing or pumping cycle which may typically cover and angle of from about 5 to about 15 degrees, or from about 7 to about 10 degrees.

In further specific embodiments in which one pumping cycle as defined above amounts to 180 degrees, the rotation angle of the first section (the section with increasing height) may be selected in the range of from about 165 to about 170 degrees, the rotation angle of the second section (the section with decreasing height) may be selected in the range of from about 0 to about 2 degrees and the rotation angle of the third section (the section with substantially constant height) may be selected within the range from about 1 to about 13 degrees, wherein the sum of the sectional rotation angles add to 180 degrees.

In yet another embodiment, the rotation angle is smaller than 0 degrees. This means that an "undercut" exists into which the respective part will fall before starting a new cycle. This allows a back-rotation which can help to clear the nozzle exit from undesired splashes or droplets and even retract liquid into the nozzle exit, so that the next dosing cycle can start from a very stable, pre-determined status, increasing quality of the device.

In another embodiment, further, a means for blocking the actuation of the inhalation device is present, adapted to inhibit a change of the relative axial position of rotatable part and counterpart corresponding to the third section. This means that the means for blocking the actuation prevents accidental release of the means for the storage of potential energy, and thus, premature emission of medical liquid through the nozzle. Only intentional deactivation of the means for blocking allows said emission.

Said device can be provided by a push-button which gives way to a further rotation only upon pushing, or by an axial indentation or bump of the third section, resulting in a mechanical obstacle that prevents further rotation due to a temporary increase of necessary rotational force, or by a retractable mechanical obstacle which prevents the movement along aforesaid "drop".

Preferably, the rotating position at which the blocking means becomes active is at the very end of the third section, or just behind said end. Thus, upon unblocking, the discharge phase can start automatically, without further manual rotation.

In one embodiment, said means for blocking the actuation is adapted to, upon its deactivation, passively allow a further rotation, or actively further rotate said part such that the second section of the cam surface comes in contact with the counterface. This embodiment is particularly advantageous if the blocking means becomes active before the end of the third section. Then, a further rotation is necessary to activate the dosing. This further rotation is then provided either manually, or actively during deactivation of the blocking device, pushing the counterface over the edge of the third section into the second section.

According to another embodiment, the means for blocking initially (i.e. when activated, engaged) blocks any relative axial motion of the rotatable part with respect to the counterpart when the counterface is in contact with the third section, i.e. prior to the emission phase. When the blocking means is deactivated, it allows said axial motion, and the emission phase starts immediately.

In summary, the blocking means can either temporarily inhibit a rotation of the rotatable part into the third section, or a linear motion along said section.

In further embodiments, the slope of the first section is selected of the group consisting of being constant, increasing, decreasing, and a combination thereof. A constant slope results in a constant increase of the pumping chamber volume. If the slope increases, the loading rate of the pumping chamber with liquid at a constant rotational speed also increases along the angle. A smooth beginning of the loading phase is the result.

If a pre-loaded check valve is present between reservoir and pumping chamber, a sharper start of the phase of filling the pumping chamber with liquid from the reservoir can be required. This can be achieved by a decreasing slope, having the highest rate at the beginning of said phase, while during the rest of the phase, the rotational force decreases.

Also, combinations of said slopes can be advantageous, depending on the concrete requirements of the construction.

The invention also relates to a method for the generation of an aerosol by means of an inhalation device according to the above definition. For the sake of conciseness, reference is made to the explanations above. In other words, all the options and preferences described for the inhalation device itself also apply to this method.

The method comprises, upon rotation of the rotatable part, a first "charging phase" for filling the pumping chamber with liquid, and a second "discharging phase" for emitting the atomized liquid from the nozzle. According to the invention, between said two phases, a third "resting phase" exists during which, despite further rotation, the volume of the pumping chamber remains constant. These three phases correspond to the aforementioned three sections. In particular, during the third phase, since there is no linear relative motion of the cylindrical part, the volume of the pumping chamber does not change.

With regard to the method of the present invention also, one dosing cycle is achieved by a rotation of 180 degrees. Thus, a rotation over 360 degrees encompasses two dosing cycles. However, in other embodiments, other integral numbers such as three or four cycles per rotation over 360 degrees are possible as well.

In a preferred embodiment, the entire resting phase is passed upon a rotation of 7±6 degrees, i.e. from about 1 to about 13 degrees.

It is clear that the remaining angle to complete one cycle (180 degrees) is available for the sum of first and second phase and the respective sections as described above in connection with the first aspect of the invention.

In specific embodiments, the term 'medically active liquid' as used herein refers to a medically active liquid in form of a pharmaceutical composition comprising at least one active pharmaceutical ingredient (API), more specifically at least one inhalable active pharmaceutical ingredient. More specifically, such at least one inhalable active pharmaceutical ingredient may, for example, be selected from long-acting muscarinic antagonists (LAMA), long-acting beta agonists (LABA) and inhalable glucocorticoids (ICS), as well as from analgetics and antidiabetics, either alone or in combination which each other.

Examples for long-acting muscarinic antagonists (LAMA) comprise, but are not limited to aclidinium bromide, glycopyrronium salts, such as glycopyrronium bromide, revefenacin, tiotropium, such as tiotropium bromide, umeclidinium bromide, oxitropium bromide, flutropium bromide, ipratropium bromide, trospium chloride, tolterodine.

Examples for long-acting beta agonists (LABA) comprise, but are not limited to, albuterol, arformoterol, bambuterol, bitolterol, broxaterol, carbuterol, clenbuterol, fenoterol, formoterol, hexoprenaline, ibuterol, indacaterol, indacterol, isoetharine, isoprenaline levosalbutamol, mabuterol meluadrine, metaproterenol, olodaterol, orciprenaline, pirbuterol, procaterol, reproterol, rimiterol, ritodrine, salmeterol, salmefamol, soterenot, sulphonterol, tiaramde, terbutaline, terbuterol.

Examples of inhalable glucocorticoids (ICS) comprise, but are not limited to, prednisolone, prednisone, butixocort propionate, flunisolide, beclomethasone, triamcinolone, budesonide, fluticasone, mometasone, ciclesonide, rofleponide, dexamethasone, etiprednol-dichloroacetat, deflazacort, etiprednol, loteprednol, RPR-106541, NS-126, ST-26.

Furthermore, active pharmaceutical ingredients may be selected from analgetics, such as opioid analgetics (e.g. morphine, fentanyl) or non-opioid analgetics (e.g. salicylic acid derivates, e.g. acetylsalicylic acid) or cannabinoids (e.g. tetrahydrocannabinol), antidiabetics, such as insulin.

The medically active liquid or liquid pharmaceutical composition that may be nebulized or aerosolized by the present inhalation device may comprise at least one active pharmaceutically ingredient as described above, but may also comprise a mixture of two or more active pharmaceutically ingredients that may be administered by inhalation.

The medically active liquid or pharmaceutical composition that may be aerosolized by the inhalation device according to the invention is preferably formulated as a composition that is suitable, and adapted for inhalative use, in other words a composition that may be nebulized or aerosolized for inhalation and that is physiologically acceptable for inhalation by a subject.

The medically active liquid or pharmaceutical composition that may be administered by the inhalation device according to this aspect of the invention or contained within the inhalation device and reservoir may be in the form of a dispersion, for example a suspension with a liquid continuous phase, and a solid dispersed phase or in the form of a solution.

In further embodiments, the medically active liquid or pharmaceutical composition as described above may comprise, optionally, one or more physiologically acceptable excipients, which are suitable for inhalative use. Excipients which may be featured in the composition may include, but are not limited to, one or more buffering agents to regulate or control pH of the solution, salts, taste-masking agents, surfactants, lipids, antioxidants, and co-solvents, which may be used to enhance or improve solubility, for example ethanol, or a glycol.

In specific embodiments, the medically active liquid as described above may be essentially free of a propellant.

In further specific embodiments, the medically active liquid as described above may be an aqueous solution, in which one or more active pharmaceutical ingredients as described above are dissolved and solubilized in a liquid carrier solution comprising water. Such aqueous solutions optionally may also comprise one or more excipients as described above.

DESCRIPTION OF FIGURES

In FIG. 1, a schematic simplified cross-sectional view of a generic inhalation device is shown. FIG. 1 shows the situation prior to first use.

Figure 1:
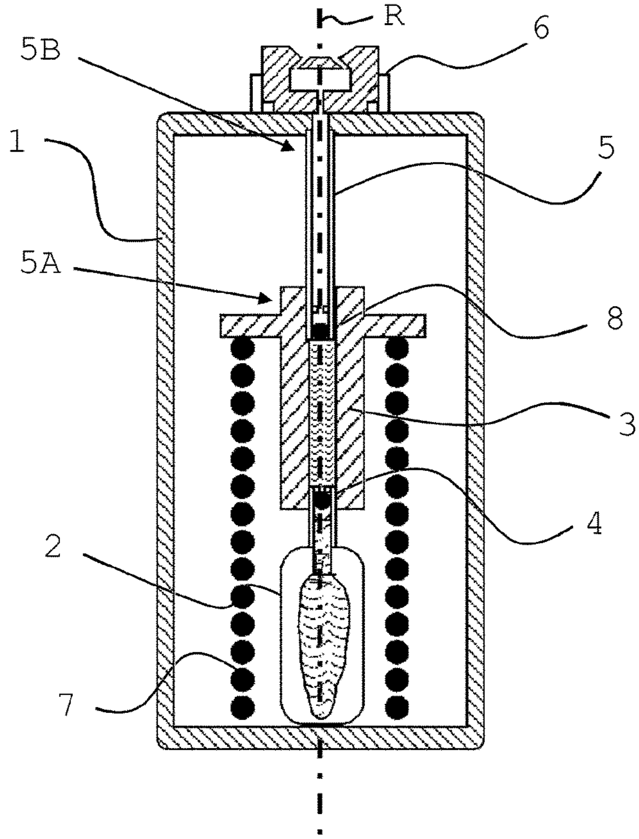
FIG. 1 shows a schematic simplified cross-sectional view of a generic inhalation device.

The inhalation device comprises a housing 1, which is preferably shaped and dimensioned such that it can be held with one hand and can be operated by one finger, e.g. the thumb (not shown). A reservoir 2 for storage of a medically active liquid is located inside the housing 1. The depicted reservoir 2 is designed to be collapsible; that means that during proceeding emptying, the elastic or at least limp walls buckle, so that the underpressure which is necessary for extraction of a certain amount of liquid is not, or almost not, increased. A similar effect can be achieved when a rigid container has a moveable bottom by means of which the interior volume of the reservoir can also be successively be reduced (not shown).

Further, the inhalation device comprises a pumping device with a hollow cylindrical part 3 forming a pumping chamber of variable volume within the housing 1 for generation of the desired pressure which is necessary for emitting liquid and nebulizing the same. The pumping device can also comprise additional, not depicted components (push button, locking device, etc.).

Hollow cylindrical part 3 is fluidically connected with reservoir 2 by means of an optional inlet check valve 4. Check valve 4 serves for allowing inflow of liquid into the pumping chamber, and blocks a back flow of liquid into reservoir 2 upon release of a not-depicted blocking means.

As a means for the storage of potential energy 7, a compression spring is provided which is coupled with one (upwards directed) end to the hollow cylindrical part 3 and which is supported at the bottom of housing 1 (lower part of the figure).

The inhalation device further comprises a riser pipe 5 with at least one reservoir-facing, upstream end portion 5A which can be received in said hollow cylindrical part 3. In other words, riser pipe 5 can at least partially be pushed into the hollow cylindrical part 3 forming the pumping chamber, resulting in a decrease of the interior volume of the pumping chamber. The term "interior volume" describes that volume which extends from the reservoir-facing inlet of the pumping chamber to the place where the interior end 5A of the riser pipe 5 is located. In the depicted situation, riser pipe 5 is almost entirely extracted from the hollow cylindrical part 3. As a result, the interior volume of the pumping chamber, presently situated between check valve 4 and the upstream end portion 5A of riser pipe 5, is at a maximum, and filled with liquid.

Preferably, in the section which serves for the reception of the riser pipe 5, hollow cylindrical part 3 has at least a section with a circular inner cross section that corresponds to the (then also) circular outside cross section of the according riser pipe section. Of course, other cross section shapes are possible as well.

According to the depicted embodiment, check valve 4 is arranged between reservoir 2 and inlet of the pumping chamber.

Also, the inhalation device comprises a nozzle 6 which is connected liquid-tight to a downstream end portion 5B of riser pipe 5. Nozzle 6 can be any known nozzle which is suitable for nebulizing/atomizing liquid. The nozzle 6 which is depicted as an example uses the principle of nebulization by means of two colliding liquid jets. Preferably, the cross sections of the liquid-containing channels are relatively small, and typically, in the region of microns.

Also depicted is an optional outlet valve 8 inside riser pipe 5 for avoiding back flow of liquid or air into the downstream end portion 5B of the same from the outside. Outlet valve 8 is arranged in the upstream end portion 5A of riser pipe 5. Liquid can pass outlet valve 8 in direction of nozzle 6, but outlet valve 8 blocks any undesired back flow in the opposite direction.

As can be seen in FIG. 1, riser pipe 5 is designed immobile and firmly attached to housing 1, indicated by the connection in the region of exterior end 5B with housing 1. Riser pipe 5 is also firmly attached to nozzle 6, which in turn is attached to housing 1 as well. On contrary, hollow cylindrical part 3 is designed to be moveable with respect to housing 1, riser pipe 5, and nozzle 6.

Not visible in FIG. 1 is the gear mechanism required according to the invention due to which the linear relative motion of the hollow cylindrical part 3 can be effected by a relative rotation around a rotational axis R of a rotatable part which is part of, or connected to, the housing 1 with respect to a second part of said housing 1, such that said relative rotation can be converted into said linear relative motion.

Figure 2:
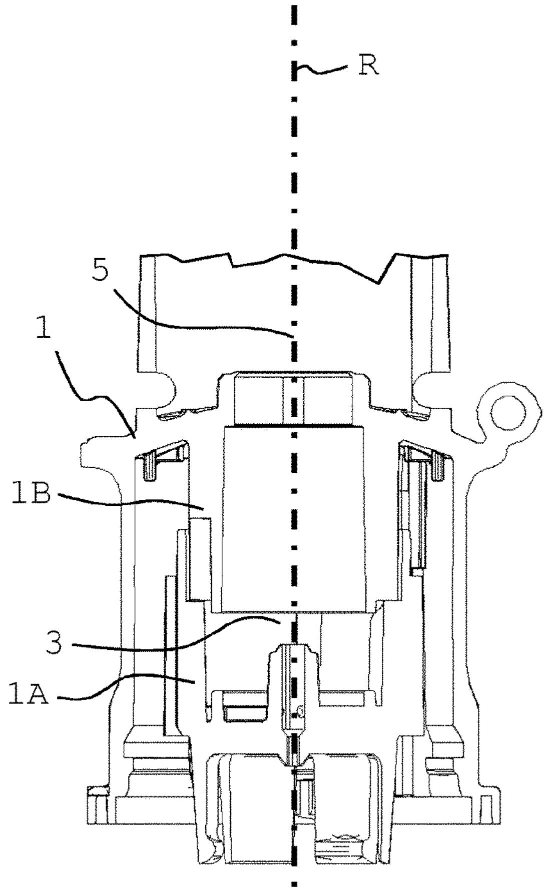
FIG. 2 shows a more detailed cross-sectional view of an inhalation device.

However, in FIG. 2, an embodiment of the invention is shown where these components are visible. Some of the reference numerals as well as the lower parts shown in FIG. 1 (means for storage of potential energy, reservoir) are omitted. The pumping chamber lies in the overlapping segments of hollow cylindrical part 3 and riser pipe 5, any valves are not shown. In particular, it can be seen how housing 1, rotatable part 1A and counterpart 1B are associated with each other. The counterpart 1B is firmly connected to the housing 1. The rotatable part 1A is partially overlapping with the counterpart 1B. The rotatable part 1A can, within certain limits, linearly move along rotational axis R. However, it does not co-rotate with counterpart 1B. Riser pipe 5 is connected to the part of the housing 1 to which the counterpart 1B is also connected, as well as to the nozzle 6 (not shown), and the hollow cylindrical part 3 is connected to the rotatable part 1A. Thus, by linearly moving rotatable part 1A, the interior volume of hollow cylindrical part 3 which forms a pumping chamber can be changed. In the present example, moving rotatable part 1A upwards (i.e. downstream, or towards the nozzle) reduces the volume, resulting in an emission of liquid, and moving downwards increases it, resulting in (re-)filling the pumping chamber from the reservoir side.

Figure 3:
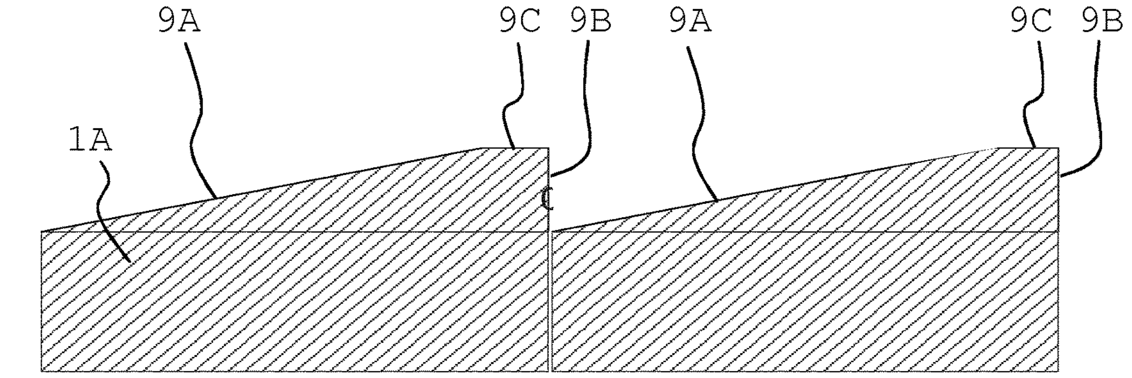
FIG. 3 shows a simplified developed view of a rotatable part with a cam surface having two series of three sections.

In FIG. 3, a simplified developed view of the rotatable part 1A having a rim with two series of cam surface sections, each of them comprising sections 9A, 9B and 9C is depicted. The rim provides a downstream surface of rotatable part 1A. Alternatively, the rim with the cam surface could be accommodated in counterpart 1B, or both the rotatable part 1A and the counterpart 1B could feature corresponding cam surfaces. It is clear that all three versions would result in the same translation of a rotation into a linear motion.

As can be seen in FIG. 3, the first section 9A consists of a rising slope, whereas third section 9C is provided by a "flat" slope. Subsequently, the second section 9B is shaped as a "step" or vertical "drop". In the depicted example, the corresponding rotation angle for one dosing cycle, i.e. a rotation from the beginning of the first section 9A until the end of the second section 9B, amounts to 180 degrees. A full 360 degree relative rotation of the rotatable part 1A with respect to the second part 1B would thus comprise two dosing cycles.

Figure 4:
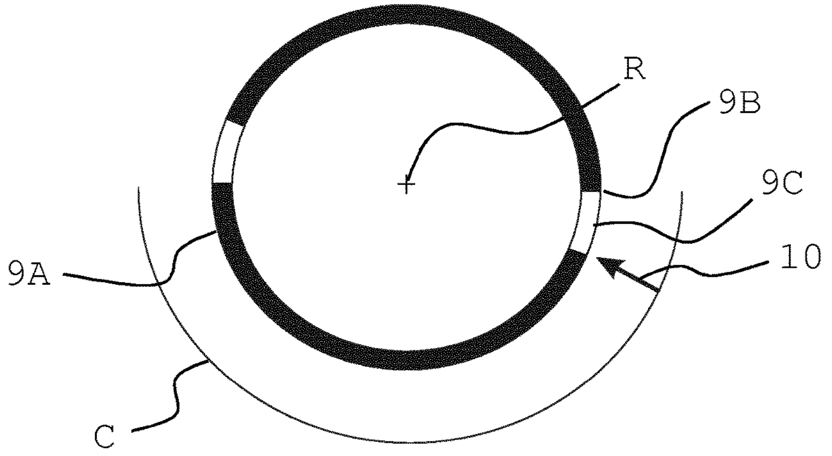
FIG. 4 shows a simplified top view of the rotatable part having two series of three sections.

FIG. 4 shows the same situation in a top view, i.e. a view parallel to the rotational axis R. Semicircle C indicates the rotation angle of one dosing cycle (180 degrees). At the beginning of said angle (leftmost starting point), the first section 9A begins. The arrow 10 indicates the beginning of third section 9C. Just between this third section 9C and the next first section (thick black line, reference numeral omitted), belonging to a second dosing cycle, lies second section 9B. In the view of the present example, second section 9B runs along the viewing direction (parallel to rotation axis R) and is therefore very short. In contrast, third section 9C has a visible length, such that, upon ongoing rotation, said section is easy to detect manually. If it is intended that the loaded device does not yet discharge a dose, the rotation is stopped anywhere on the third section. When further rotated, the end of third section 9C is reached, and the device is actuated while the counterpart (not shown) glides over the edge of first section 9A and drops along second section 9B. Then, a new cycle can begin.

Figure 5:
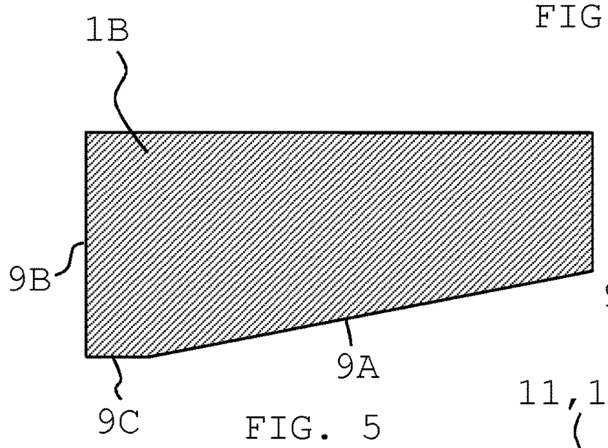
FIGS. 5, 6 and 7 show a schematic simplified developed view of a counterpart with a counterface.
Figure 6:
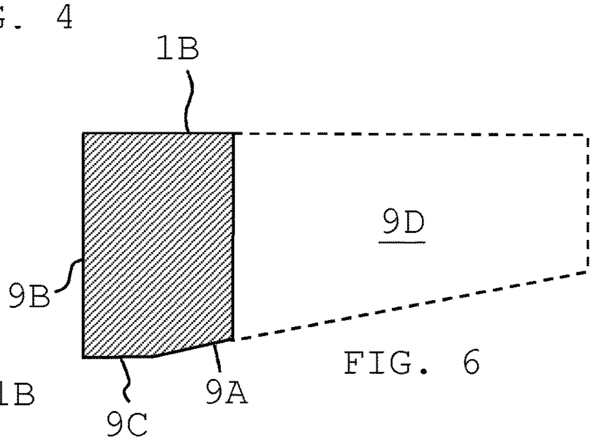
Figure 7:
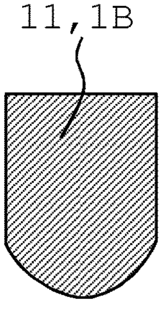

FIGS. 5 to 7 show the counterface which is, in the depicted embodiment, a feature of the counterpart 1B. Alternatively, or additionally, it can be a feature of the rotatable part 1A as well. In FIG. 5, the counterface has the inverted shape of the cam surface shown in FIG. 3, carrying all three sections 9A, 9B, 9C.

In FIG. 6, the counterface is shortened; however, it still has a flat part, which corresponds to third section 9C, as well as a sloping part corresponding to first section 9A. At the right-hand side of FIG. 6, the area drawn in dashed lines indicates the fourth section 9D which "interrupts", or shortens, the corresponding first section 9A. However, the remaining counterface is sufficient for the desired cam interaction between the two surfaces/components 1A, 1B.

FIG. 7 shows a short cam 11 which is also sufficient for the desired interaction, but provides a low area of overlap between sections 9A, 9B, 9C (not shown) and its counter face (not shown).

Figure 8:
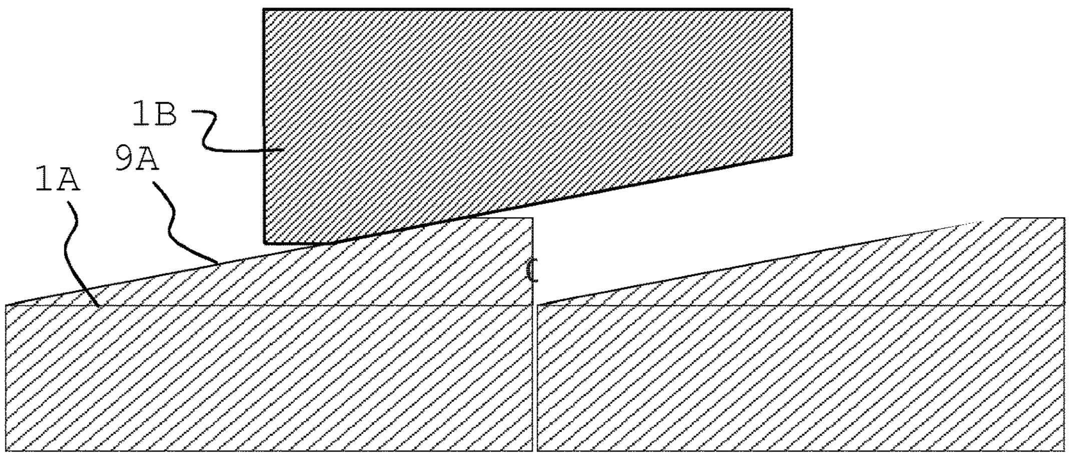
FIGS. 8, 9 and 10 show different stages of interaction between cam surface and counterface.
Figure 9:
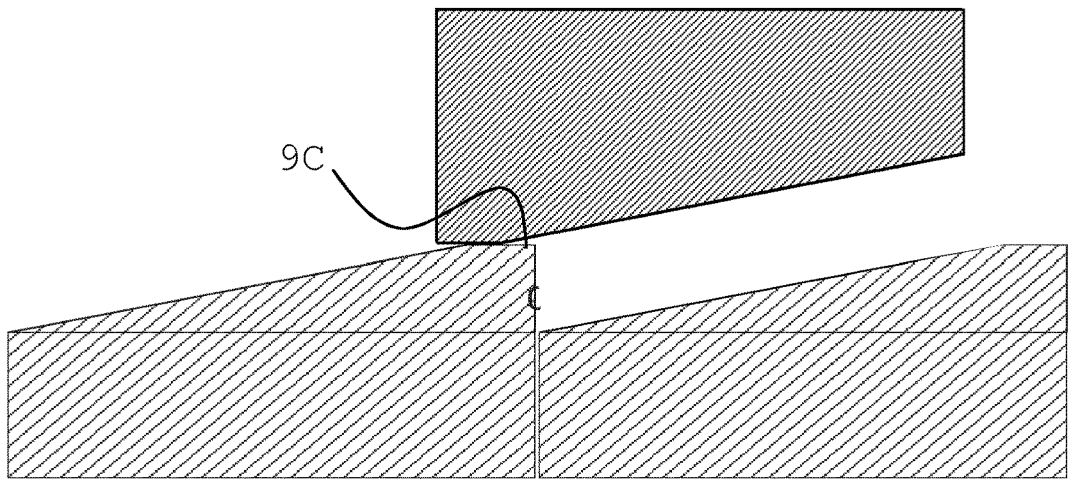
Figure 10:
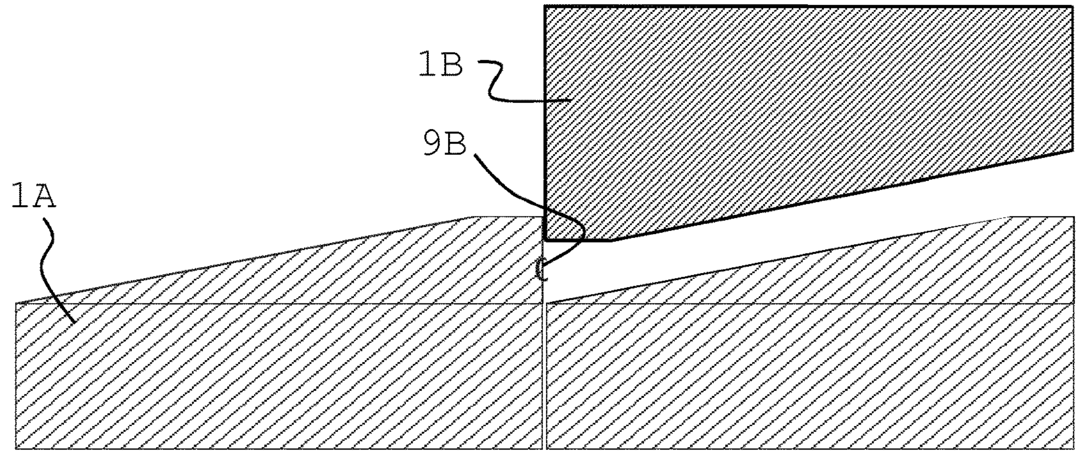

In FIGS. 8, 9 and 10, different stages of interaction between cam surface and counterface are shown. In this embodiment, both parts 1A, 1B have, for each section 9A, 9B and 9C, matching shapes or slopes of the respective cam surfaces; of course, one has the inverted silhouette of the other. Like parts have like reference numerals (partially omitted). A relative rotation of the actual parts 1A, 1B is depicted by a relative motion in the figures; a relative movement of the counterpart 1B to the right corresponds to the intended rotation direction (loading, resting, discharging).

In FIG. 8, the loading phase is shown, wherein counterpart 1B glides on first section 9A of rotatable part 1A, resulting in a linear movement of counterpart 1B such as to increase the volume of the pumping chamber (not shown) and load the means for the storage of potential energy (not shown).

In FIG. 9, the resting phase is depicted, wherein, despite a possible further rotation, no change of volume and loading takes place, since the axially measured distance (or axial position) of parts 1A and 1B remains constant.

In FIG. 10, said distance decreases rapidly, since counterpart 1B "drops" down along the second section 9B of rotatable part 1A. Thus, this figure depicts the discharging phase.

Subsequently, the device is at the beginning of another dosing cycle that will start with the loading situation.

Figure 11:
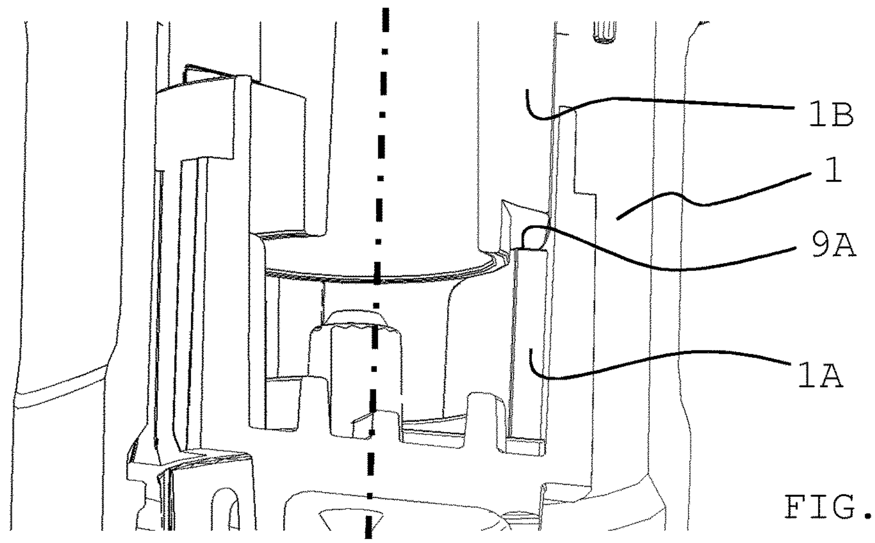
FIGS. 11, 12 and 13 show views of a more detailed embodiment which is in the respective stages that correspond to FIGS. 8, 9 and 10.
Figure 12:
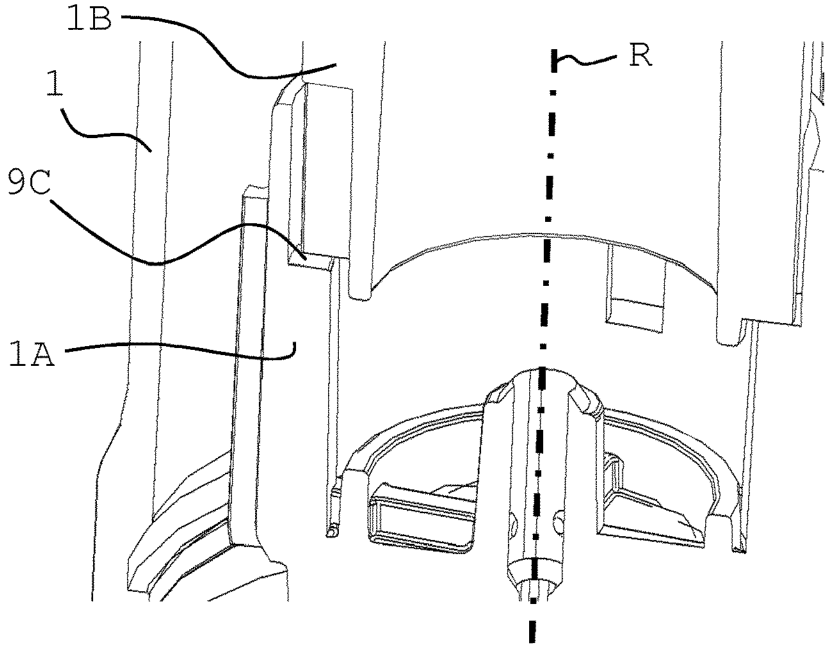
Figure 13:
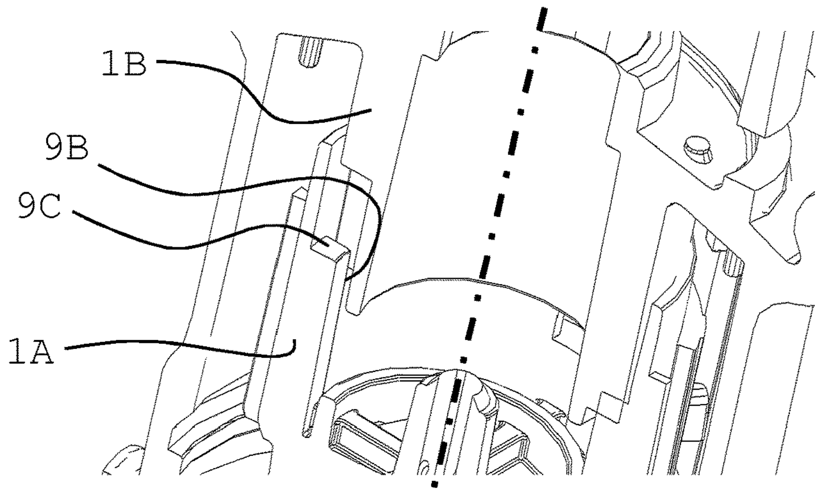

The subsequent drawings FIGS. 11, 12 and 13 correspond to the phases which are schematically depicted in previous FIGS. 8, 9 and 10.

Note that in the depicted embodiment, a rotation of 180 degrees results in a complete dosing cycle, comprising loading and discharging phase. Further note that, in order to make the relevant regions as well visible as possible, the sectional views do not have identical sectional planes.

In FIG. 11, the device is in the loading phase. Counterpart 1B is firmly connected to a part of the housing 1. Rotatable part 1A provides the cam surface. In the depicted phase, sloping section 9A is in contact with the adjacent counterface of counterpart 1B.

In FIG. 12, the resting phase is depicted. In this situation, section 9C (flat section) is in contact with the corresponding counterface. Further rotation around rotational axis R would not (immediately) result in change of the axial position or distance between rotatable part 1A and counterpart 1B.

In FIG. 13, finally, the discharging phase is shown. In this phase, "dropping" section 9B slides along the corresponding counterface, and the distance between rotatable part 1A and counterpart 1B rapidly decreases, driven by the means for the storage of energy (not shown) which now releases its energy to put the pumping chamber (not shown), putting the same under pressure. As a result, liquid is emitted from the nozzle (both not shown).

Figure 14:
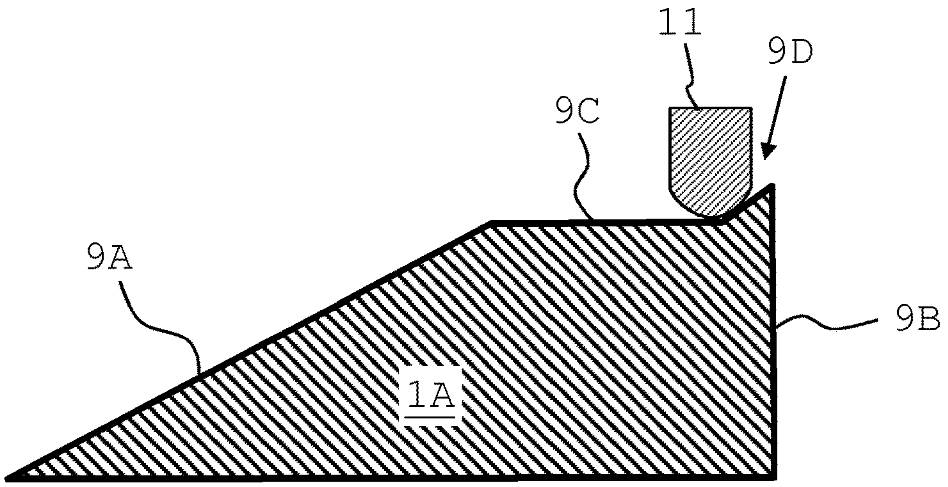
FIGS. 14, 15 and 16 show examples of a fourth section intended to inhibit further rotation of the rotatable part.
Figure 15:
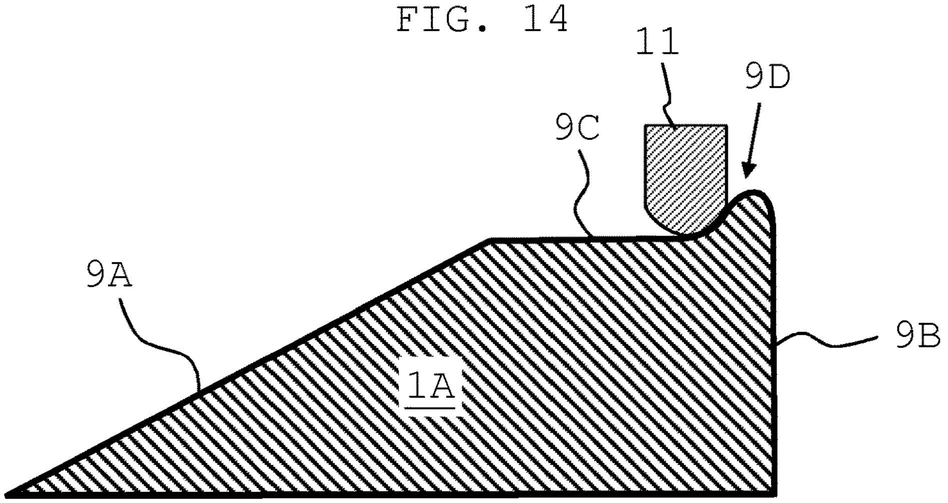
Figure 16:
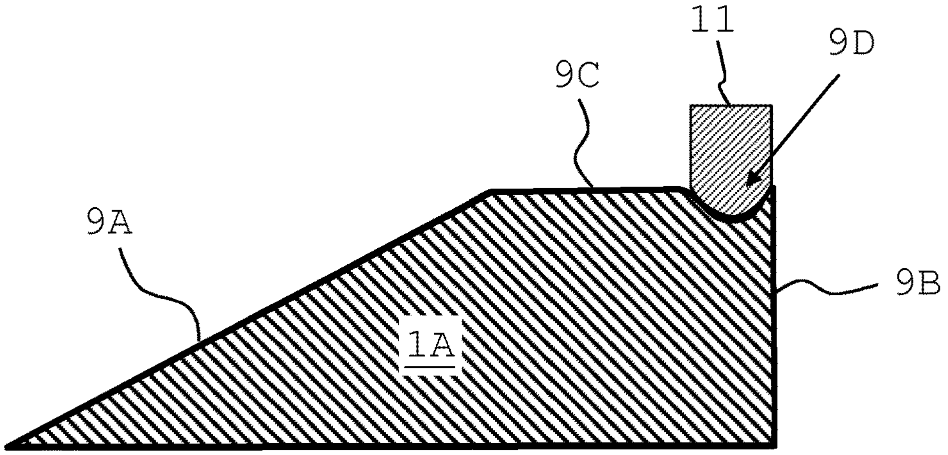

In FIGS. 14, 15 and 16, not-to-scale examples of a fourth section 9D intended to inhibit further rotation of the rotatable part are shown.

In these embodiments, fourth section 9D is arranged at the end of section 9C. According to FIG. 14, the fourth section 9D is provided with a slope of increasing height. Therefore, when the counterface which is represented by a cam 11 arrives, upon rotation, at the fourth section 9D, climbing said section would require to further charge the means for the storage of potential energy (not shown). However, the user will be able to sense this sudden increase in force needed for further rotation and stop in further rotate. Also, without other external force, the rotation will as well not proceed, making sure that e.g. during storage, no unintentional release of liquid will occur.

In FIG. 15, the fourth section 9D fulfills the identical function. In this embodiment, it has a shape of a firstly increasing and then decreasing slope ("bump"). Only when the highest point is passed, the emission phase starts.

In FIG. 16, the fourth section 9D provides a firstly decreasing and then increasing slope ("notch"). When the cam reaches the lowest portion of the fourth section 9D, is rests in this stable position until additional force is provided in order to "lift" it out of said section for the emission to start.

Compared to an embodiment without a fourth section 9D, such as shown in FIGS. 8-10 which feature a rotational angle of the third section 9C of "original", full size, the rotational angle of the fourth section covers a percentage from 5% to 50%, or from 10% to 30%, or from 15% to 25%, of said "original" angle, respectively. The maximum height (or depth, respectively) of the fourth section 9D with respect to the third section 9C amounts to a value from 0.05 mm to 5 mm, or from 0.1 mm to 1 mm, or from 0.25 mm to 0.5 mm.

LIST OF REFERENCES

1 housing
1A rotatable part
1B counterpart
2 reservoir
3 hollow cylindrical part
4 check valve
5 riser pipe
5A upstream end portion
5B downstream end portion
6 nozzle
7 means for the storage of potential energy
8 outlet valve
9A first section
9B second section
9C third section
9D fourth section
10 arrow
11 cam
R rotational axis
C semicircle The following list of numbered items are embodiments comprised by the present invention:

1. Inhalation device for medically active liquids (F) for generation of an aerosol, comprising
   a housing (1), inside this housing (1) a reservoir (2) for storing a liquid (F), a pumping unit, said unit comprising a riser pipe (5), a hollow cylindrical part (3) having an interior space configured to receive an upstream end portion (5A) of said riser pipe (5), said cylindrical part (3) being linearly moveable on the riser pipe (5), wherein the cylindrical part (3) and the riser pipe (5) form a pumping chamber having, by means of linear relative motion of the cylindrical part (3) with respect to the riser pipe (5), a variable volume for generation of a pressure inside said pumping chamber, wherein the pumping chamber is fluidically connected with the reservoir (2) and with a nozzle (6) which is connected liquid-tight to an downstream end portion (5B) of the riser pipe (5),
   and wherein said linear relative motion can be effected by a relative rotation around a rotational axis (R) of a rotatable part (1A) which is part of, or connected to, a first part of the housing (1) with respect to a counterpart (1B) which is part of, or connected to, a second part of said housing (1), such that said relative rotation is converted into said linear relative motion by means of a gear mechanism, said gear mechanism comprising at least one cam surface having, in axial direction, a first section (9A) of increasing height as well as a second section (9B) of decreasing height, the cam surface being capable of sliding along an adjacent counterface, wherein the cam surface is, upon rotation, adapted to slide along said counterface, resulting in said conversion,
   and wherein a means for the storage of potential energy (7) is provided which is chargeable by means of said relative rotation along the first section (9A), and wherein said energy is releasable to said pumping device when released,
   characterized in that said cam surface has, between the first section of increasing height (9A) and the second section of decreasing height (9B), a third section (9C) of constant height, such that, while said third section (9C) of said cam surface slides along the counterface, no linear relative motion occurs.
2. Inhalation device according to item 1, wherein
   the cam surface is arranged at, or connected to, the rotatable part (1A), and the counterpart (1B) provides the counterface, or
   the cam surface is arranged at, or connected to, the counterpart (1B), and the rotatable part (1A) provides the counterface.
3. Inhalation device according to item 1 or 2, wherein the counterface is provided by a second cam surface, or a cam (11), or a roller.
4. Inhalation device according to any of items 1 to 3, wherein a dosing cycle which covers the rotation angle of the first, the second, and the third section (9A, 9B, 9C), corresponds to a rotation of 360 degrees, or to a whole-number fraction thereof.
5. Inhalation device according to item 4, wherein the sum of the rotation angles as defined in claim 4 amounts to 180 degrees.
6. Inhalation device according to item 5, wherein the rotation angle of the third section (9C) amounts to 7±6 degrees.
7. Inhalation device according to any of the preceding items, wherein the rotation angle of the second section (9B) amounts to 0 degrees, resulting in an axially oriented section of the cam surface.
8. Inhalation device according to any of the preceding items, wherein further a means for blocking the actuation of the inhalation device is present, adapted to inhibit a change of the relative axial position of rotatable part (1A) and counterpart (1B) corresponding to the third section (9C).
9. Inhalation device according to item 8, wherein said means for blocking the actuation is adapted to, upon its deactivation, passively allow a further rotation, or actively further rotate the rotatable part (1A) such that the second section (9B) of the cam surface comes in contact with the counterface, or allow a previously blocked relative axial motion of the rotatable part (1A) with respect to the counterpart (1B), corresponding to the second section (9B).

10. Inhalation device according to any of the preceding items, wherein the slope of the first section (9A) is selected of the group consisting of being constant, increasing, decreasing, and a combination thereof.

11. Method for the generation of an aerosol by means of an inhalation device according to any of the preceding items, wherein the method comprises, upon rotation of the rotatable part (1A), a first, charging phase for filling the pumping chamber with liquid, and a second, discharging phase for emitting the atomized liquid from the nozzle (6), characterized in that between said two phases, a third, resting phase exists during which, despite further rotation, the volume of the pumping chamber remains constant.

12. Method according to item 11, wherein one dosing cycle is achieved by a rotation of 180 degrees.

13. Method according to item 11 or 12, wherein the entire resting phase is passed upon a rotation of 7±6 degrees.

What is claimed is:

1. An inhalation device for medically active liquids for generation of an aerosol, comprising:

a housing, inside the housing a reservoir for storing a liquid, a pumping unit, said pumping unit comprising a riser pipe, a hollow cylindrical part having an interior space configured to receive an upstream end portion of said riser pipe, said cylindrical part being linearly moveable on the riser pipe, wherein the cylindrical part and the riser pipe form a pumping chamber having a variable volume for generation of a pressure inside said pumping chamber due to linear relative motion of the cylindrical part with respect to the riser pipe, wherein the pumping chamber is fluidically connected with the reservoir and with a nozzle which is connected liquid-tight to a downstream end portion of the riser pipe, and wherein said linear relative motion is configured to be caused by a relative rotation around a rotational axis of a rotatable part which is part of, or connected to, a first part of the housing with respect to a counterpart which is part of, or connected to, a second part of said housing with a gear mechanism configured to convert said relative rotation into said linear relative motion, said gear mechanism comprising at least one cam surface comprising, in an axial direction corresponding to a longitudinal axis of the pumping chamber, a first section of increasing height as well as a second section of decreasing height, the at least one cam surface configured to slide along an adjacent counterface, wherein the at least one cam surface is, during said relative rotation, configured to slide along said counterface, resulting in said conversion, and wherein a potential energy storage device is provided which is configured to be charged by said relative rotation along the first section, and wherein said energy is configured to be released to said pumping unit when released, and wherein the at least one cam surface comprises, between the first section of increasing height and the second section of decreasing height, a third section of constant height, such that, while said third section of the at least one cam surface slides along the counterface, no linear relative motion of the cylindrical part with respect to the riser pipe occurs, and wherein a dosing cycle which covers the rotation angle of the first, the second, and the third section, corresponds to a rotation of 180 degrees.

2. The inhalation device according to claim 1, wherein the at least one cam surface is arranged at, or connected to, the rotatable part, and the counterpart provides the counterface, or the at least one cam surface is arranged at, or connected to, the counterpart, and the rotatable part provides the counterface.

3. The inhalation device according to claim 1, wherein the counterface is provided by a second cam surface, or a cam, or a roller.

4. The inhalation device according to claim 1, wherein the rotation angle of the third section amounts to 7±6 degrees.

5. The inhalation device according to claim 1, wherein the rotation angle of the first section is selected in the range of from about 165 to about 170 degrees, the rotation angle of the second section is selected in the range of from about 0 to about 2 degrees and the rotation angle of the third section is selected within the range from about 1 to about 13 degrees, wherein a sum of rotation angles of the first section, second section, and third section adds up to 180 degrees.

6. The inhalation device according to claim 1, wherein the at least one cam surface further comprises a fourth section of decreasing or increasing height between the third section and the second section.

7. The inhalation device according to claim 6, wherein the at least one cam surface further comprises a constant height section following the second section.

8. The inhalation device according to claim 1, wherein the at least one cam surface further comprises a constant height section following the second section.

9. The inhalation device according to claim 1, wherein the rotation angle of the second section amounts to 0 degrees, resulting in an axially oriented section of the at least one cam surface.

10. The inhalation device according to claim 1, further comprising a means for blocking actuation of the inhalation device, the means for blocking actuation of the inhalation device configured to inhibit a change of the relative axial position of the rotatable part and the counterpart corresponding to the third section.

11. The inhalation device according to claim 10, wherein said means for blocking actuation of the inhalation device is configured to, upon deactivation of the means for blocking actuation of the inhalation device, passively allow a further rotation, or actively further rotate the rotatable part such that the second section of the at least one cam surface comes in contact with the counterface, or allow a previously blocked relative axial motion of the rotatable part with respect to the counterpart, corresponding to the second section.

12. The inhalation device according to claim 1, wherein a slope of the increasing height of the first section is selected from the group consisting of being constant, increasing, decreasing, and a combination thereof.

13. A method for the generation of an aerosol by the inhalation device according to claim 1, wherein the method comprises, upon rotation of the rotatable part, a first, charging phase for filling the pumping chamber with liquid, and a second, discharging phase for emitting the atomized liquid from the nozzle, wherein between said two phases, a third, resting phase exists during which, despite further rotation, the volume of the pumping chamber remains constant.

14. The method according to claim 12, wherein the third, resting phase is passed upon a rotation of 7±6 degrees.

* * * * *